(12) United States Patent
Bellemere et al.

(10) Patent No.: US 8,647,390 B2
(45) Date of Patent: Feb. 11, 2014

(54) INTRAMEDULLARY ANCHORING STEM FOR AN ORTHOPAEDIC IMPLANT HEAD

(75) Inventors: Philippe Bellemere, Nantes (FR); Thierry Dreano, Rennes (FR); Jean Goubau, Loppem (BE); Xavier Martinache, Reims (FR); Michaël Papaloïzos, Geneva (CH); Bernard Prandi, Rennes (FR); Pierre Siret, Talensac (FR); Alain Tchurukdichian, Dijon (FR)

(73) Assignee: Memometal Technologies (FR)

( * ) Notice: Subject to any disclaimer, the term of this patent is extended or adjusted under 35 U.S.C. 154(b) by 165 days.

(21) Appl. No.: 12/918,189

(22) PCT Filed: Jan. 8, 2010

(86) PCT No.: PCT/FR2010/000011
§ 371 (c)(1),
(2), (4) Date: Dec. 8, 2010

(87) PCT Pub. No.: WO2010/079289
PCT Pub. Date: Jul. 15, 2010

(65) Prior Publication Data
US 2011/0077652 A1 Mar. 31, 2011

(30) Foreign Application Priority Data
Jan. 8, 2009 (FR) ...................................... 09 00053

(51) Int. Cl.
*A61F 2/42* (2006.01)
(52) U.S. Cl.
USPC ......................................... 623/21.16; 606/63

(58) Field of Classification Search
USPC .............. 623/21.11, 21.15–21.17; 606/62, 63
See application file for complete search history.

(56) References Cited

U.S. PATENT DOCUMENTS

| | | |
|---|---|---|
| 3,745,590 A | 7/1973 | Stubstad |
| 3,909,853 A | 10/1975 | Lennox |
| 3,924,276 A | 12/1975 | Eaton |
| 4,180,871 A | 1/1980 | Hamas |
| 4,242,759 A | 1/1981 | White |
| 4,250,873 A | 2/1981 | Bonnet |
| 4,451,254 A | 5/1984 | Dinius et al. |
| 4,453,930 A | 6/1984 | Child |
| 4,725,280 A | 2/1988 | Laure |
| 4,732,564 A | 3/1988 | Potucek et al. |
| 4,865,605 A | 9/1989 | Dines et al. |
| 4,944,758 A | 7/1990 | Bekki et al. |
| 4,955,916 A | 9/1990 | Carignan et al. |
| 4,959,065 A | 9/1990 | Arnett et al. |

(Continued)

FOREIGN PATENT DOCUMENTS

| | | |
|---|---|---|
| DE | 2424537 A1 | 12/1974 |
| DE | 29721522 U1 | 2/1998 |

(Continued)

*Primary Examiner* — Ellen C Hammond
(74) *Attorney, Agent, or Firm* — Lerner, David, Littenberg, Krumholz & Mentlik, LLP

(57) ABSTRACT

An intramedullary anchoring stem for an orthopaedic implant head. The stem is in one piece, is made of biocompatible material and is movable in relation to the head, with which it has connecting means, and it has a truncated or substantially truncated peg shape at least partially recessed longitudinally, and parallel or substantially parallel to the dorso-palmar plane.

18 Claims, 3 Drawing Sheets

(56) References Cited

U.S. PATENT DOCUMENTS

| | | |
|---|---|---|
| 5,047,059 A | 9/1991 | Saffar |
| 5,228,455 A | 7/1993 | Barcel |
| 5,358,529 A | 10/1994 | Davidson |
| 5,387,244 A | 2/1995 | Breard |
| 5,405,399 A | 4/1995 | Tornier |
| 5,405,401 A * | 4/1995 | Lippincott et al. ......... 623/21.15 |
| 5,425,777 A | 6/1995 | Sarkisian |
| 5,507,822 A | 4/1996 | Bouchon et al. |
| 5,702,458 A | 12/1997 | Burstein et al. |
| 5,702,469 A | 12/1997 | Whipple et al. |
| 5,728,163 A | 3/1998 | Maksene |
| 5,782,927 A * | 7/1998 | Klawitter et al. ......... 623/21.15 |
| 6,572,534 B1 | 6/2003 | Milbocker et al. |
| 6,622,864 B1 | 9/2003 | Debbs et al. |
| 6,699,292 B2 | 3/2004 | Ogilvie et al. |
| 6,811,568 B2 | 11/2004 | Minimikawa |
| 6,887,169 B2 | 5/2005 | Whitehill et al. |
| 7,004,946 B2 | 2/2006 | Parker et al. |
| 7,182,787 B2 | 2/2007 | Hassler et al. |
| 7,347,130 B2 | 3/2008 | Pham et al. |
| 7,491,209 B2 | 2/2009 | Mueller et al. |
| 7,507,252 B2 | 3/2009 | Lashinski et al. |
| D610,686 S | 2/2010 | Klawitter et al. |
| D619,718 S | 7/2010 | Gannoe et al. |
| 7,803,162 B2 | 9/2010 | Marnay et al. |
| 7,837,739 B2 | 11/2010 | Ogilvie |
| 7,857,851 B2 | 12/2010 | Zannis et al. |
| 2003/0040805 A1* | 2/2003 | Minamikawa ............. 623/23.46 |
| 2008/0154385 A1* | 6/2008 | Trail et al. .................. 623/21.15 |
| 2010/0010637 A1 | 1/2010 | Pequignot |
| 2011/0106269 A1* | 5/2011 | Warburton ................. 623/21.15 |

FOREIGN PATENT DOCUMENTS

| | | |
|---|---|---|
| DE | 19820748 A1 | 11/1999 |
| DE | 19925529 A1 | 12/2000 |
| EP | 0524874 A1 | 1/1993 |
| EP | 1632200 A | 3/2006 |
| FR | 2670109 A1 | 6/1992 |
| FR | 2680967 A1 | 3/1993 |
| FR | 2734150 A1 | 11/1996 |
| FR | 2736818 A | 1/1997 |
| FR | 2736818 A | 1/1997 |
| FR | 2743717 A1 | 7/1997 |
| FR | 2912051 A1 | 8/2008 |
| GB | 2049435 A | 12/1980 |
| GB | 2251795 A | 7/1992 |
| WO | 0243627 A2 | 6/2002 |

* cited by examiner

INTRAMEDULLARY ANCHORING STEM FOR AN ORTHOPAEDIC IMPLANT HEAD

CROSS REFERENCE TO RELATED APPLICATIONS

This application is the US national phase of PCT application PCT/FR2010/000011, filed Jan. 8, 2010, published Jul. 15, 2010 as WO2010/079289, and claiming the priority of French patent application 0900053 itself filed Jan. 8, 2009, whose entire disclosures are herewith incorporated by reference.

The present invention relates to an intramedullary anchor stem for an orthopedic implant head used in digital arthroplasty.

It also relates to a method of installing such a stem.

It finds a particularly important, albeit nonexclusive, application in the medical field of prostheses of the interphalangeal proximal joint of the hand (known in the field by the initials IPP).

But it is also more generally applicable to the joints between other types of phalange, referred to as proximal, and a distal adjacent phalange.

The term proximal phalange refers to a phalange or metatarsal or metacarpal bone element located toward the body or limb (hand or foot), and the term distal phalange to a phalange located outward of this limb, according to the orientation conventions conventionally adopted in anatomy, and which will be used hereinafter.

The invention can also be used for interphalangeal digital articular prostheses of the thumb (thumb IP) or for interphalangeal distal prostheses (IDP) of the hand or foot.

It can also advantageously be used for metacarpophalangeal digital articular prostheses (called MCP), trapeziometacarpal (called TMC), here again of the hand or foot, by simple geometric adaptation to the relative bone sites.

Interphalangeal articular prostheses comprising first and second elements, each having a respective stem for implantation in the bone and an additional interphalangeal joint head, are already known.

For example, it is known from (EP 1,339,362) [US 20080154385] to have an implant comprising a first element provided with a head having a convex, bicondylar joint surface and a second element provided with an additional head.

The elements of such prostheses are constituted of one piece, the stem having the shape of a full peg affixed to the head and arranged so as to be inserted inside the medullary cavity of a phalange.

The problem solved by this type of prosthesis is that of wear of the articular surfaces, the stem itself being considered as secondary.

Prostheses comprising conical anchor stems that are elongated about an axis are also known (EP 1870061) [US 2008/0154385].

Here again, the problem of wear of the prosthesis is strictly solved due to the complementary interfit of the joint surfaces.

Also known (US 2003/0040805) [U.S. Pat. No. 6,811,568] are three-part prostheses, namely a head, a spacing piece, and a hollow stem whose end has the shape of a duck's bill forming two flexible, deformable, strips between a position of insertion into the bone and an anchoring position where the spacing piece blocks the prosthesis. Such a system is complicated to implement.

The object of the present invention is to provide an orthopedic implant and a method that meet the requirements of the art better than those previously known, particularly as the invention causes only a very slight wear despite numerous articular movements and is very simple and easy to mount while adapting to the constraints related to the ulterior functions of arthroplasty joints.

To do so, it notably stems from a different approach from that used in the prior art.

Rather than taking for granted the necessity of a full and solidly rigid implant stem, to ensure the anchoring of an joint whose wear is thus limited by the adoption of a particular shape of heads, the present invention has first accepted the reconsideration of the very design of the stem affixed to the head.

First, it has thus made it separable from the head, which notably allows the use of two different materials and the replacement of the head without having to remove the stem.

The invention therefore provides a one-piece stem adapted to be implanted, without screwing, in the intramedullary channel of the bone.

The invention has finally, and in combination with this dissociation and the one-piece rigid connection, made the stem itself more flexible in the dorsal-palmar plane by proposing a stem having an apparent elasticity and rigidity close to the bone in which it is implanted.

These elements all together give a more natural behavior of the heads against one another, having as unforeseen consequence that of considerably limiting their wear while having the advantages of the known one-piece elements in terms of solidity, that is, without the fragility and the complexity of the multipart implants of the prior art.

In other words, the invention enables a range of intramedullary anchor stems of great solidity to be provided, but whose deformations under constraint are equivalent to those of the bones in the sagittal plane (anterior-posterior); a plane according to which physiological constraints are predominantly transmitted when the joint is placed under weight-bearing conditions (pinching, grabbing . . . ).

The constraint phenomena called "stress-shielding" associated with rigidity differences between the bone and the prosthetic pieces are thus minimized, favoring osteointegration of the intramedullary stem.

To this end, the present invention proposes for an orthopedic implant head an intramedullary anchor stem that is fixed with respect to the head by releasable connecting means, the stem comprising a body at least in part longitudinally recessed, parallel or substantially parallel to the dorsal-palmar plane, characterized in that the stem is formed in one piece by the body, and in that it has a tapered or substantially tapered peg shape made of biologically compatible material.

Thanks to this modularity, with a stem shape lightened in the dorsal-palmar plane, the latter being made of a predetermined biologically compatible material, the stem is thus more flexible in this plane and more fittable with the respective phalanges, which limits the wear of the prosthesis while allowing the bone to grip the stem better and in a less traumatic manner.

In a particularly advantageous way, the longitudinally grooved portion is arranged so as to provide the stem, in a predetermined shape and material, with elasticity and/or rigidity corresponding to predetermined values that are close to those of a bone, and particularly of a finger or toe bone.

The predetermined values can be chosen by one having ordinary skill in the art as a function of the particular characteristics of the bone of the patient to be treated, as described hereinafter with reference to Young's modulus to be "effective" or apparent.

Advantageous embodiments further call for one and/or the other of the following provisions:

the stem has a radius greater than zero of curvature set so as to fit to the inside of the medullary cavity of a phalange;

it has a sink-preventing end abutment;

the stem is at least partially grooved, and its material, provide it with an effective Young's modulus $E_{eff} < 30$ Gpa;

The term effective or apparent Young's modulus refers to an overall Young's modulus of the stem whose behavior is identical to that of bone.

In practice, to calculate the effective Young's modulus such as envisioned in the present invention, the bone is equated to a cortical tube having a Young's modulus on the order of 20 Gpa, the spongy part thus participating little or not at all to the resistance.

This tubular bone is then transformed into a homogeneous material, that is of solid construction that thus has the effective Young's modulus.

For example, for a young bone (≤35 years), the thickness of the tube is on the order of 1.5 mm and the effective Young's modulus of the full stem is thus on the order of 16 Gpa.

For an elderly person, the thickness of the cortical sheath is closer to 1 mm and the equivalent modulus is on the order of 13 Gpa.

The effective or apparent Young's modulus of the stem is thus the combination between the intrinsic modulus and a geometric factor:

the effective Young's modulus is $E_{eff} < 20$ Gpa, for example 16 Gpa;

the effective Young's modulus is $E_{eff} < 15$ Gpa, for example 12 or 13 Gpa;

the stem is of H-section;

it is of U- or V-section;

it has a slot shaped like a duck's bill in the dorsal-palmar plane;

it has a semicylindrical grooved shape on the palmar side, or is semitubular;

the connecting means are formed by a conical interfit between a pin fixed to the head and a recess in the corresponding stem. The recess is complementary to the pin;

the stem is asymmetrical with respect to a median plane passing through the axis of the recess, parallel to the dorsal-palmar plane;

the conical fitting is a Morse taper, which means that the taper of the angle is on the order of 5%; but this taper can also be less, for example on the order of 3% or 2.5%;

the connecting means between the stem and the corresponding head further comprises a recess or a groove formed in one of the parts shaped to receive a small plate of complementary shape fixed to the other part;

the stem comprises, at least in part, an osteointegration coating strengthening its anchoring;

the stem is made of microporous titanium and/or is coated with hydroxyapatite;

the stem is formed out with at least one recess transversely or substantially transversely crossing the stem.

The invention further proposes an implant comprising an intraphalangeal joint head comprising a stem such as described above.

Advantageously, the material of the stem is different from the material of the joint head.

More precisely, two rigidities, apparent or effective Young's modulus of stems, different depending on the patients, can be provided: a rigid stem for young patients (i.e. less than about 30 GPa), and a more flexible stem for elderly patients (i.e. less than about 15 GPa), the head being made of polyethylene having a Young's modulus smaller, for example by <5 Gpa, for example 2 Gpa.

Finally, the invention proposes an assembly of implants for which the connecting means are identical between, on the one hand, several differently sized heads and, on the other hand, identical or different stems of first elements and/or of second elements.

Such provision allows great modularity.

The invention also proposes a method of installing an orthopedic implant stem for a digital arthroplasty of the type described above.

It will be better understood from reading the following description of embodiments given hereinafter by way of non-limiting examples. The description refers to the accompanying drawings, in which:

FIG. 1 is a top schematic view of a hand 1 of a skeleton, having orthopedic implant stems 2 according to the invention.

Figure 1:
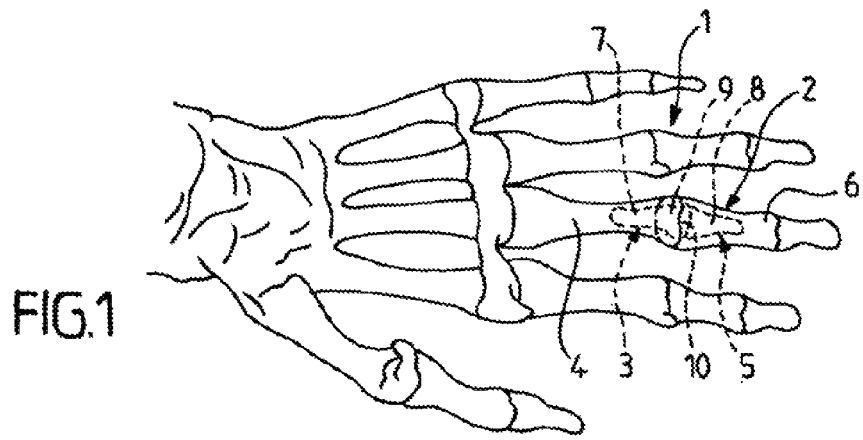
FIG. 1 is a top, schematic view, of a hand skeleton in which implant stems according to the invention have been installed.

The implant comprises a first element 3 for a proximal phalange 4 and a second element 5 for a distal phalange 6.

The elements comprise respective stems 7 and 8 for implantation or anchoring into the bone, as well as interphalangeal joint heads 9 and 10.

The same references will be used to represent similar or identical elements.

Figure 2:
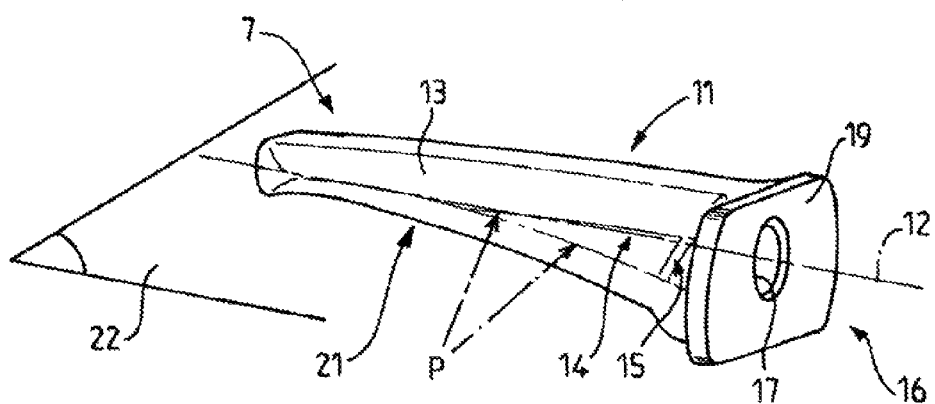
FIG. 2 is a perspective view of an implant stem according to a first embodiment of the invention.

FIG. 2 shows the removable anchor stem 7 for the head 9 of the first element 3 (see FIG. 3) made of biocompatible material, for example titanium.

It comprises an elongated portion 11 extending substantially along an axis 12, slightly curved, for example with a 100 mm radius of curvature p for a stem of a large-size proximal element, and 90 mm for an average- or small-size proximal element, or comprised between 50 mm (large), 40 mm (medium), and 10 mm (small) for the distal elements.

The stem is provided with a portion 13 shaped so as to be insertable in the central hole of the shaft of the phalange, in a shape that is substantially polygonal and tapered, for example hexagonal with an enlarged end part 14 having a facet 15 allowing for a good insertion and lateral blocking in indexation in the modular cavity of the phalange.

The stem 7 is removably mounted with respect to the head and comprises means 16 for connection to the head.

These connection means comprise a conical socket 17 in which a conical pin 18 (cf. FIG. 5A), that is fixed to the head 9, is fitted, for example a Morse taper or having an angle, tapered by 2 or 3°.

The pin and the recess have complementary shapes and cooperate frictionally with one another.

The stem further comprises a sink-preventing small plate 19 that cooperates with a complementary recess in the form of a groove 20 (see FIG. 3), that enables a good joining and a good indexing of the head 9 of the stem 7 while the pin 18 is pushed in the socket 17 and the small plate 19 is blocked in the recess 20.

According to the invention, the stem 7 further comprises at least one recessed part 21 in the dorsal-palmar plane 22, which provides it with the desired flexibility and which will be described in detail hereinafter.

Figure 3:
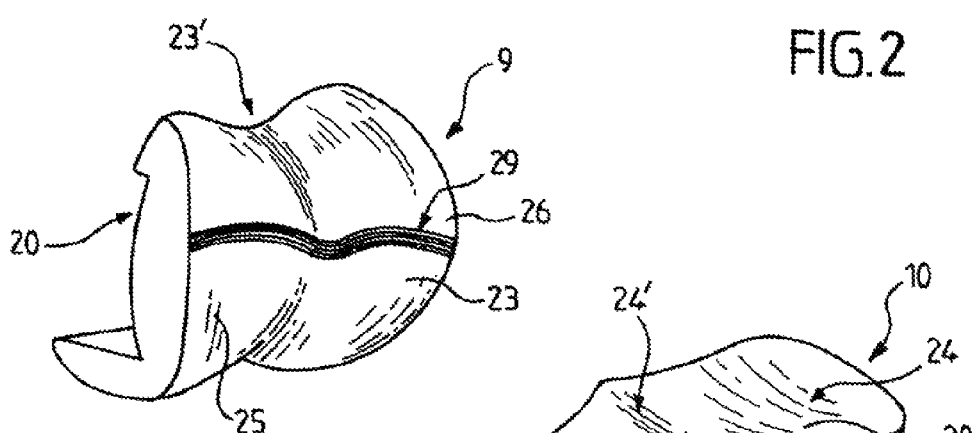
FIGS. 3 and 4 are perspective views of examples of biconvex and biconcave heads designed to be able to fit with the stem of FIG. 2.

FIG. 3 shows the head 9 of the first element 3.

It has a biconvex condylar joint surface 23 comprising a central valley 23'.

Figure 4:
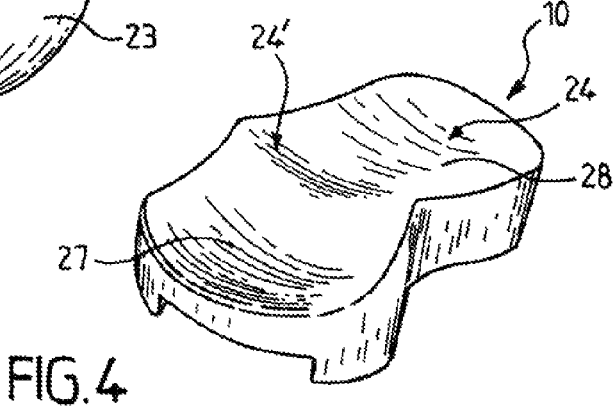

FIG. 4 shows the head 10 of the second element.

The latter has a biconcave surface 24 arranged so as to cooperate with the biconvex surface 21 of the head of the first element and is provided with a central crest 24'.

The surfaces 23 and 24 are made, for example, so as to be congruent in the area of the two condyles 25 and 26 and of the corresponding concave surfaces 27 and 28 in the front plane of the joint and non-congruent in the sagittal plane.

But any other type of head can be considered.

FIG. 3 shows the contact surface obtained with a head of first element made of elastic material when a longitudinal pressure is exerted.

Indeed, the friction line in the frontal plane transforms into a surface 29, which makes it possible to better distribute the friction forces and thus eventually to minimize wear of the head.

Due to the combination of the material of this head that can, for example, be a polymer of the UHMWPE type, of the respective radii of curvature described above, and of the characteristics of the invention, further enhanced damping and minimized wear of the prosthesis, long-term, are thus obtained.

In this regard, it can be noted that the contact area 29 sweeps half of the condyle but stays at about the same place on the distal portion.

Advantageously, the most fragile surface is then chosen on the condyle side, the flexibility of the stems in the dorsal-palmar plane allowing wear that is even better distributed as described above.

Figure 5A:
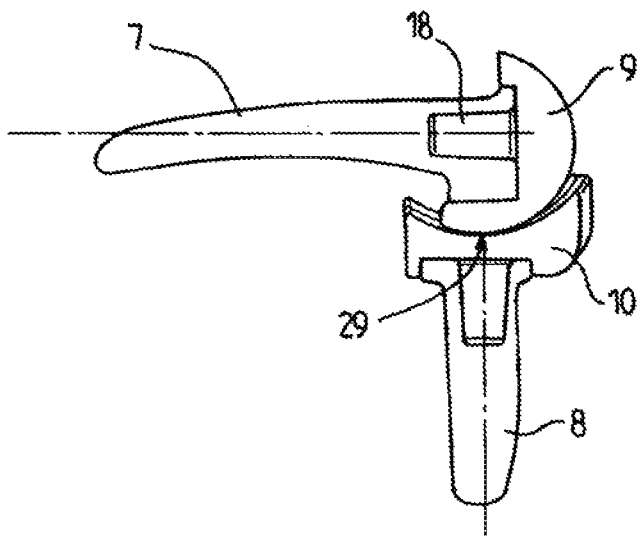
FIGS. 5A and 5B are cross-sectional drawings of the joint in the flexed-finger and straight-finger positions, respectively, showing the flexibility of the stems designed for minimizing wear of the joint surfaces.
Figure 5B:
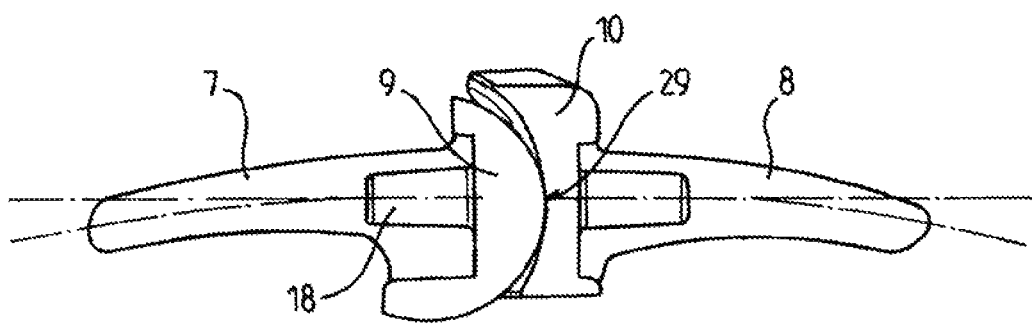

FIGS. 5A and 5B show the evolution of the flexibility of the stems 7 and 8 during movement between flexed-finger (FIG. 5A) and straight-finger (FIG. 5B) positions.

Making the dimensions of the pins 18 and of the sockets 17 uniform and standard allows a head of a certain dimension to be matched to stems of different dimension, which provides great modularity.

Other mechanical mounting means of the head on the stem are, of course, possible.

Figure 6:
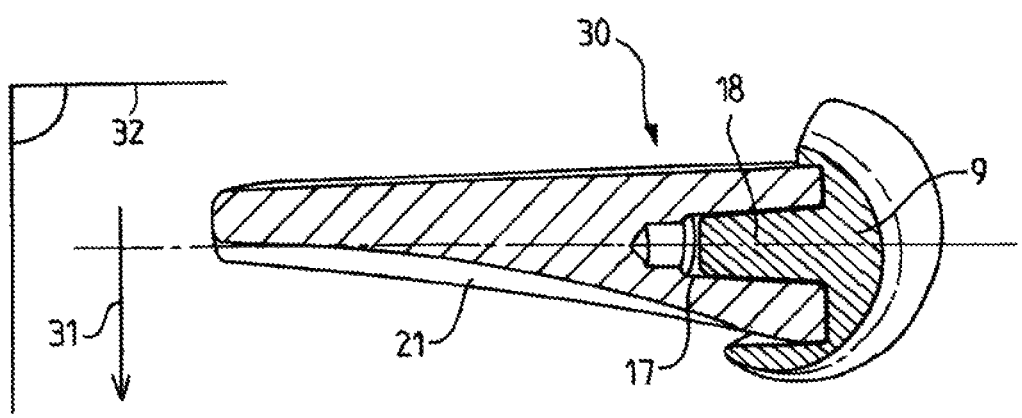
FIG. 6 is a side cross-sectional view of an implant element comprising a stem and a head according to an embodiment of the invention.

FIG. 6 is a cross-sectional view of a first element 30 comprising the head 9 and the stem 7, the pin 18 being force-fitted inside the socket 19 [17].

The recess 21 allows good flexibility (arrow 31) in a plane 32 perpendicular to a dorsal-palmar plane 22.

FIGS. 7 to 11 show stems for a distal or proximal element having different shapes and lengths depending on different embodiments of the invention.

Figure 7:
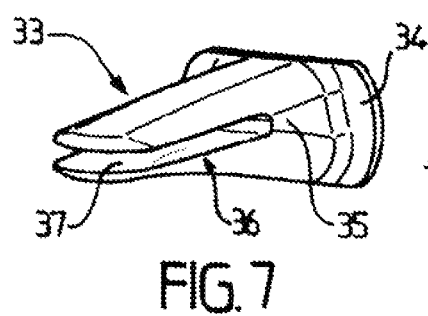
FIGS. 7 to 11 are a rear perspective views of five embodiments of the implant stem according to the invention.

The stem 33 of FIG. 7 has at one end a sink-preventing plate 34 of the type described with reference to FIG. 2, formed with a socket for receiving the pin of the head.

A solid part 35 extends in the direction opposite to the plate from a flat beveled portion 36 provided with a slot 37 opening out over its entire length of small thickness, for example 2 mm in the dorsal-palmar plane, which gives it a normal duck's bill shape.

Figure 8:
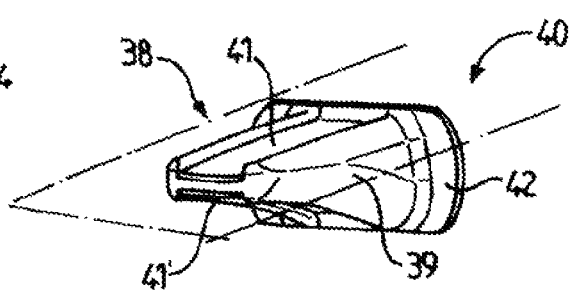

FIG. 8 shows another embodiment of the stem 38 having a portion 39 designed to be pushed inside the bone, substantially pyramidal or tapered, and having an H-section, thus freeing on both sides of a dorsal-palmar plane 40, substantially parallelepiped-shaped recesses 41 from the bill-shaped end 41['] to the sink-preventing plate 42.

Figure 9:
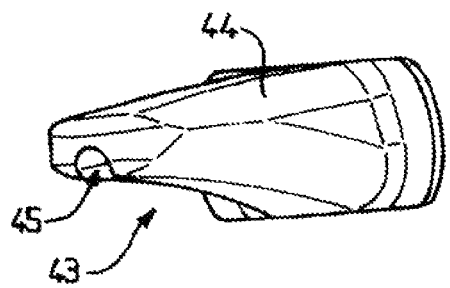

FIG. 9 shows another stem 43 comprising a tapered portion 44 provided on its lower surface with a groove 45 giving the stem a ⅔ recessed shape along $9/10^{th}$ of its length.

Figure 10:
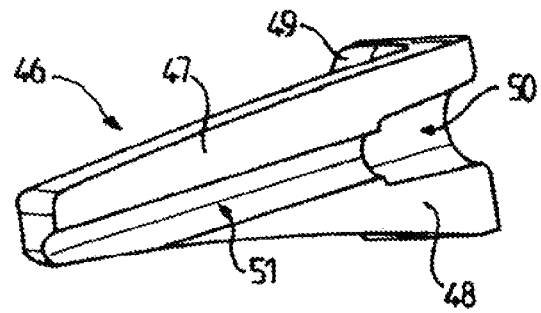

FIG. 10 shows the cross-section of a half stem 46 in the shape of a substantially cylindrical tube 47 comprising an end portion 48 provided with the plate 49 pierced with a recess 50 so as to cooperate with the pin of the head, as previously described, the recess 50 being extended with a bore 51 over the entire length of the tube 47.

Figure 11:
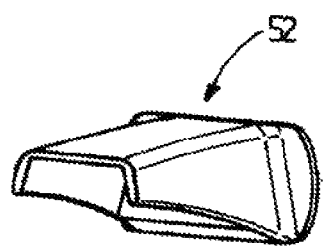

FIG. 11 shows a stem 52 in the shape of a bent sheet, is having an end portion 53 of U-section.

In the embodiments of the invention more particularly described here, the stems are rough.

This roughness is, for example, obtained by sand blasting or grit-blasting, or by transverse grooves (not shown), allowing the bone to better adhere.

In order to further improve anchoring, an osteointegration coating, for example of the hydroxyapatite (HAP) or formed in microporous titanium by plasma deposits, is advantageously provided.

The installation of a prosthesis according to the invention during implant surgery will now be described.

After the finger has been opened up and the damaged bone parts have been cut so as to install the prosthesis, in a manner known in itself, (first step of bone resection), the holes for the stems are prepared (insertion of rasps), then the fixation stem is inserted into the medullary channel.

The available space for installing the heads is then checked, then the condylar proximal head 9 is nested, the head being fixed with precision and blocked by means of the Morse taper of the stem.

A test is then carried out with a model of the other distal head.

Then, after the thickness has been chosen as a function of the prior resection of the bone, the stem 8 is installed on the other side in the distal phalange and the joint is then finalized by setting the respective head 10 in place.

The fact that the head 10 can be chosen with several different thicknesses for its base enables adjustment during surgery.

The entire operation is carried out in a manner known in itself by means of dedicated ancillary equipment.

It goes without saying and it also results from what precedes that the present invention is not limited to the embodiments more particularly described. On the contrary, it encompasses all the variations and particularly those where the anchor stems are not made of metal, in biocompatible polyethylene, for example, or are made in a metal other than titanium, those where the prosthesis is an IP thumb or big toe prosthesis, or an IPD or metacarpophalangeal prosthesis, which involves different dimensions and a different drawing of articular surfaces in order to enable appropriate lateral mobility.

The invention claimed is:

1. An orthopedic implant comprising:
   an implant head including a head body and a pin, the body and the pin defining a groove; and
   an intramedullary anchor stem fixable to and separable from the implant head, the stem including:
   a stem body having the shape of a tapered or substantially tapered peg; and
   a plate on an end of the stem body, the plate having a flat face in a plane and a thickness extending in a transverse direction from the plane, the flat face and thickness being received within the groove of the implant head, the flat face surrounding an aperture defined by the plate for receiving the pin of the implant head, the aperture having an axis therethrough and extending into the end of the stem body, wherein the flat face is perpendicular to the aperture axis and extends a full width of the stem body, the width of the stem body being in a direction perpendicular to the axis.

2. The orthopedic implant according to claim 1, wherein a longitudinally recessed portion extends at least partially into the stem body to form a cavity therein so as to provide the stem, whose shape and material have been predetermined, with elasticity or rigidity corresponding to predetermined values close to those of a bone.

3. The orthopedic implant according to claim 1, wherein the stem is substantially elongated along an axis and has a radius of curvature greater than zero so as to fit inside the medullary cavity of a phalange.

4. The orthopedic implant according to claim 1, wherein the flat plate is a sink-preventing end abutment.

5. The orthopedic implant according to claim 1, wherein the stem body has a shape that is at least partially grooved around the aperture axis and is made of a material that provides it with an effective Young's modulus $E_{eff} < 30$ Gpa.

6. The orthopedic implant according to claim 5, wherein the stem body has an effective Young's modulus $E_{eff} < 15$ Gpa.

7. The orthopedic implant according to claim 1, wherein the stem body is of H-section.

8. The orthopedic implant according to claim 1, wherein the stem body is of U- or V-section.

9. The orthopedic implant according to claim 1, wherein the stem body has a slot shaped like a duck's bill in a dorsal-palmar plane.

10. The orthopedic implant according to claim 1, wherein the stem body has a recessed shape that is semicylindrical or semitubular on a palmar side.

11. The orthopedic implant according to claim 1, wherein the stem body is asymmetrical with respect to a median plane passing through an axis of the aperture, parallel to a dorsal-palmar plane.

12. The orthopedic implant according to claim 1, wherein the stem body has, at least partially, an osteointegration coating strengthening the anchoring.

13. The orthopedic implant according to claim 1, wherein the stem body is made of microporous titanium or is coated with hydroxyapatite.

14. The orthopedic implant according to claim 1, wherein the stem body is cut out with at least one recess transversely or substantially transversely crossing the stem.

15. The orthopedic implant according to claim 1, wherein the head is made of a different material than the stem.

16. A set of orthopedic implants, each orthopedic implant of the set of orthopedic implants according to claim 1, the set of the orthopedic implants comprising identical connecting means between several heads of different size and identical or different stems.

17. The orthopedic implant according to claim 1, wherein the stem body is at least partially recessed longitudinally parallel or substantially parallel to a dorsal-palmar plane.

18. The orthopedic implant according to claim 1, wherein the stem body is made of biologically compatible material.

* * * * *